(12) United States Patent
Hua et al.

(10) Patent No.: US 7,056,732 B2
(45) Date of Patent: Jun. 6, 2006

(54) **METHOD FOR ENHANCING SOLUBILITY OF RECOMBINANT PROTEIN PRODUCTS IN *E. COLI***

(75) Inventors: Zichun Hua, Jiangsu (CN); Hongxia Zhang, Jiangsu (CN)

(73) Assignee: Nanjing University, Nanjing (CN)

( * ) Notice: Subject to any disclaimer, the term of this patent is extended or adjusted under 35 U.S.C. 154(b) by 434 days.

(21) Appl. No.: 10/235,478

(22) Filed: Sep. 4, 2002

(65) Prior Publication Data

US 2003/0104628 A1    Jun. 5, 2003

(30) Foreign Application Priority Data

Sep. 5, 2001   (CN)   ................ 01 1 27171

(51) Int. Cl.
*C12N 15/00*   (2006.01)
*C12N 15/09*   (2006.01)
*C12N 15/63*   (2006.01)
*C12N 15/70*   (2006.01)
*C12N 15/74*   (2006.01)

(52) U.S. Cl. .................................. 435/320.1
(58) Field of Classification Search ............. 435/320.1
See application file for complete search history.

(56) References Cited

OTHER PUBLICATIONS

Gallie et al. The 5'-leader se1uence of tobacco masaic virus RNA enhances the expression of foreign gene transcripts in vitro and in vivo Nucleic Acids Research vol. 15 No. 8 1987 pp. 3257-3273.*

Ausubel et al. (Short Protocols in Molecular Biology 1999 pp. 10-76 to 10-80 and 16-24 to 16-27.*

"Nucleotide Sequence at the 5' Extremity of Tobacco-Mosaic-Virus RNA", Richards et wl., Eur. J. Biochem. 84, 513-519 (1978).

"Identification of the motifs within the tobacco mosaic virus 5'-leader responsible for enhancing translation", Gallie et al., Nucleic Acids Research, vol. 20, No. 17, 4631-4638.

"pALEX, a dual-tag prokaryotic expression vector for the purification of full-length proteins", Panagiotidis et al., Gene, 164 91995) 45-47.

* cited by examiner

*Primary Examiner*—James Ketter
*Assistant Examiner*—Konstantina Katcheves
(74) *Attorney, Agent, or Firm*—Merchant & Gould P.C.

(57) ABSTRACT

The present invention relates to the field of biotechnology. The invention provides a novel approach using tobacco mosaic virus omega leader sequence to enhance the solubility of the recombinant products in *E. coli* and the method of use therefore. The invention provides the utilization of tobacco mosaic virus omega leader sequence into *E. coli* expression vector, and the tobacco mosaic virus omega leader sequence containing expression vector can be used in combination with other available means to obtain higher expression or better solubility. The invention can be applied to biotechnological pharmaceutical industry, genetic engineering, biochemistry and molecular biology etc. The invention provides an expression vector pTORG, which is a highly efficient GST fusion expression vector, and can significantly enhance the yield of biologically active recombinant products.

9 Claims, 1 Drawing Sheet

SEQUENCE LISTING

```
<160> NUMBER OF SEQ ID NOS: 5

<210> SEQ ID NO 1
<211> LENGTH: 1035
<212> TYPE: DNA
<213> ORGANISM: Artificial Sequence
<220> FEATURE:
<221> NAME/KEY: misc_feature
<222> LOCATION: (1)..(1035)
<223> OTHER INFORMATION: core regulatory region of pTORG

<400> SEQUENCE: 1
taatacgact cactataggg gaattgtgag cggataacaa ttcccctcta gatatttta      60 caacaattac caacaacaca aacaacaaac aacattacaa ttactattta caataacaat    120
ggctagaaat aattttgttt aactttaaga aggagatata ccatggaaac agtattcatg    180
tcccctatac taggttattg gaaaattaag ggccttgtgc aacccactcg acttcttttg    240
gaatatcttg aagaaaaata tgaagagcat ttgtatgagc gcgatgaagg tgataaatgg    300
cgaaacaaaa agtttgaatt gggtttggag tttcccaatc ttccttatta tattgatggt    360
gatgttaaat taacacagtc tatggccatc atacgttata tagctgacaa gcacaacatg    420
ttgggtggtt gtccaaaaga gcgtgcagag atttcaatgc ttgaaggagc ggttttggat    480
```

-continued

```
attagatacg gtgtttcgag aattgcatat agtaaagact ttgaaactct caaagttgat      540
tttcttagca agctacctga aatgctgaaa atgttcgaag atcgtttatg tcataaaaca      600
tatttaaatg gtgatcatgt aacccatcct gacttcatgt tgtatgacgc tcttgatgtt      660
gttttataca tggacccaat gtgcctggat gcgttcccaa aattagtttg tttttaaaaaa     720 cgtattgaag ctatcccaca aattgataag tacttgaaat ccagcaagta tatagcatgg      780
cctttgcagg gctggcaagc cacgtttggt ggtggcgacc atcctccaaa atcggatctg      840
atcgaaggtc gtgggatccc cgggaattcg agctccgtcg acaagcttgc ggccgcactc      900
gagcaccacc accaccacca ctgagatccg gctgctaaca aagcccgaaa ggaagctgag      960
ttggctgctg ccaccgctga gcaataacta gcataacccc ttggggcctc taaacgggtc     1020
ttgaggggtt ttttg                                                      1035

<210> SEQ ID NO 2
<211> LENGTH: 66
<212> TYPE: DNA
<213> ORGANISM: Tobacco mosaic virus

<400> SEQUENCE: 2
tatttttaca acaattacca acaacacaaa caacaaacaa cattacaatt actatttaca       60
ataaca                                                                 66

<210> SEQ ID NO 3
<211> LENGTH: 131
<212> TYPE: DNA
<213> ORGANISM: Artificial Sequence
<220> FEATURE:
<221> NAME/KEY: misc_feature
<222> LOCATION: (1)..(131)
<223> OTHER INFORMATION: upstream sequence of GST coding region
<220> FEATURE:
<221> NAME/KEY: misc_feature
<222> LOCATION: (7)..(72)
<223> OTHER INFORMATION: omega leader sequence
<220> FEATURE:
<221> NAME/KEY: misc_feature
<222> LOCATION: (104)..(109)
<223> OTHER INFORMATION: ribosome binding site & SD sequence

<400> SEQUENCE: 3
tctagatatt tttacaacaa ttaccaacaa cacaaacaac aaacaacatt acaattacta       60
tttacaataa caatggctag aaataatttt gtttaacttt aagaaggaga tataccatgg      120
aaacagtatt c                                                          131

<210> SEQ ID NO 4
<211> LENGTH: 84
<212> TYPE: DNA
<213> ORGANISM: Artificial Sequence
<220> FEATURE:
<221> NAME/KEY: misc_feature
<222> LOCATION: (1)..(84)
<223> OTHER INFORMATION: downstream sequence of GST coding region
<220> FEATURE:
<221> NAME/KEY: misc_feature
<222> LOCATION: (1)..(12)
<223> OTHER INFORMATION: coding region of Factor Xa cleavage site
<220> FEATURE:
<221> NAME/KEY: misc_feature
<222> LOCATION: (14)..(63)
<223> OTHER INFORMATION: multiple cloning sites
<220> FEATURE:
<221> NAME/KEY: misc_feature
<222> LOCATION: (64)..(81)
<223> OTHER INFORMATION: coding region of histidine tag
```

-continued

```
<400> SEQUENCE: 4
atcgaaggtc gtgggatccc cgggaattcg agctccgtcg acaagcttgc ggccgcactc    60
gagcaccacc accaccacca ctga                                          84

<210> SEQ ID NO 5
<211> LENGTH: 308
<212> TYPE: DNA
<213> ORGANISM: Homo sapiens

<400> SEQUENCE: 5
caagcgaatt cgatggtcct gcttccagat gtagagactc cttccgaaga agactgtatg    60
tttgggaatg ggaaaggata ccgaggcaag agggcgacca ctgttactgg gacgccatgc   120
caggactggg ctgcccagga gccccataga cacagcattt tcactccaga gacaaatcca   180
cgggcgggtc tggaaaaaaa ttactgccgt aaccctgatg gtgatgtagg tggtccctgg   240
tgctacacga caaatccaag aaaactttac gactactgtg atgtccctca gtgtgcggcc   300
ctcgagcg                                                           308
```

METHOD FOR ENHANCING SOLUBILITY OF RECOMBINANT PROTEIN PRODUCTS IN *E. COLI*

FIELD OF THE INVENTION

The present invention relates generally to the field of biotechnology and specifically to an *E. coli* expression vector comprising an omega leader sequence between the promoter region and ribosome binding site and method for preparation thereof.

BACKGROUND OF THE INVENTION

The *E. coli* expression system is extensively used as the first choice in genetic engineering due to its high productivity, high growth and production rate, ease of use, and economy, etc. However when expressed in *E. coli*, most recombinant proteins deposit in the form of insoluble and inactive inclusion bodies. Although insoluble inclusion bodies can bring some convenience for the isolation process, biological activities of such inclusion bodies can be recovered only after in vitro process of denaturation and subsequent renaturation. In vitro renaturation is a complicated and low-efficient process. For proteins with multiple disulfide bonds, especially for pharmaceutical use, the removal of misfolded or partially misfolded proteins will bring more difficulties to the downstream purification process. Researchers usually attempt to improve the solubility or folding of recombinant proteins by a variety of means, such as co-expression of chaperone proteins, protein disulfide isomerase, or peptidyl-prolyl cis-trans isomerase and so on in vivo, growing the cells at lower temperatures, and using solubilizing fusion partners. Another commonly used method is fusion expression, by which the solubility and yield of target protein could be improved with the help of its fused partner, which is already known to be expressed well and highly soluble in *E. coli*. Most of the successful fusion protein systems are those employing glutathione S transferase (GST), *E. coli* maltose binding protein malE and *E. coli* thioredoxin (Trx). The fusion partner often provides a distinct biochemical property which can be exploited as an affinity tag for fusion protein purification. All the above mentioned alternatives have been widely applied to both academic research and pharmaceutical industry.

DISCLOSURE OF THE INVENTION

The purpose of the present invention is to provide a method of efficient avoidance or reduction of inclusion bodies formation in *E. coli*, which enriches the knowledge, means of improving solubility of recombinant products in the *E. coli* system.

The purpose of the invention can be achieved by the following method, which comprises introducing the leader sequence at 5'-UTR (untranslatable region) of tobacco mosaic virus (TMV) genome into an *E. coli* expression vector, between the promoter region and the ribosome binding site (rbs), thereby forming a novel expression vector which increases the yield of soluble, biologically active recombinant products and effectively avoids or improves the formation of inclusion bodies of recombinant proteins.

In the first aspect, the invention provides an *E. coli* expression vector comprising an omega leader sequence between the promoter region and ribosome binding site.

In a preferred embodiment, the omega leader sequence comprises the sequence of SEQ ID NO: 2.

In a preferred embodiment, said expression vector comprises a core regulatory region having the sequence of SEQ ID NO: 1.

In a preferred embodiment, said expression vector is a GST fusion expression vector.

In the second aspect, the invention provides an *E. coli* comprising the *E. coli* expression vector of the invention.

In the second aspect, the invention provides a method for improving an *E. coli* expression vector comprising the steps of:

(a) providing an *E. coli* expression vector which comprises an promoter region and ribosome binding site;

(b) inserting an omega leader sequence between said promoter region and ribosome binding site, thereby forming an expression vector which comprises said omega leader sequence.

In a preferred embodiment, said method further comprises the step of:

(c) inserting the GST coding sequence, the multiple cloning sites, and the histidine tag coding region orderly into said vector, downstream of the ribosome binding site, thereby forming a GST fusion expression vector.

The expression vector of the present invention containing omega ($\Omega$) leader sequence can be used in combination with other available methods, for example, compatible plasmids pLysS, pLysE or plasmids containing genes encoding chaperones or protein disulfide isomerase (PDI) etc., so as to inhibit the leaky expression of recombinant target proteins, improve the solubility of target products and reduce the formation of inclusion bodies. One example of the omega leader sequence is shown in SEQ ID NO: 2.

In an embodiment of this invention, the expression plasmid pTORG was constructed by interposing omega leader sequence between the promoter region and the rbs site, and by introducing the GST coding region and the multiple cloning sites into pET-32a (a commercial expression plasmid produced by Novagen Company). The regulatory core region of the plasmid, including the GST coding sequence, contains 1035 base pairs. The sequence of said regulatory core region is shown in SEQ ID NO: 1.

Since the expression vector pTORG comprises a GST coding sequence just upstream of multiple cloning sites, the present invention also provides a GST fusion expression vector. It is a high efficient GST fusion expression plasmid proved by data from several examples of GST fusion expression, e.g., GST-K5.

A main characteristic of the invention is to achieve a new *E. coli* expression vector by introducing a leader sequence derived from plant virus into a common *E. coli* expression vector. Moreover, compared with the common vector, the improved vector shows similar attributes and capacity of expression with enhanced solubility and folding efficiency, thus yielding more active products. The invention can be used as a universal, efficient, and convenient method for the various common *E. coli* expression systems. The invention, with effectively avoiding and reducing formation of inclusion bodies, thus resulting improved yield of active recombinant proteins, can be applied to bio-engineered pharmaceutical industry, genetic engineering and biochemistry and molecular biology studies.

Heterologous genes regulated by the new vector were induced for expression, and the resulting proteins exist mostly in soluble and active form, and thus the new vector successfully circumvented and reduced formation of the inclusion bodies. The expression vector containing omega leader sequence could be employed combinatively with other available expression means, for instance, to use together with LysS and LysE *E. coli* expression strain to prevent leaky expression, to transform together into *E. coli* cell with compatible plasmids containing molecular chaperon gene and/or disulfide isomerase gene and to co-express them for the purpose of improving protein solubility and reducing inclusion bodies.

1: *E. coli* colE1 replica origin; 2: Lac I gene; 3: T7 promoter; 4: omega leader sequence; 5: ribosome binding site and Shine-Dalgarno sequence; 6: Glutathione S transferase encoding gene; 7: multiple cloning sites and His6 coding region; 8: f1 replica origin; 9: ampicillin resistance gene.

Figure 2:
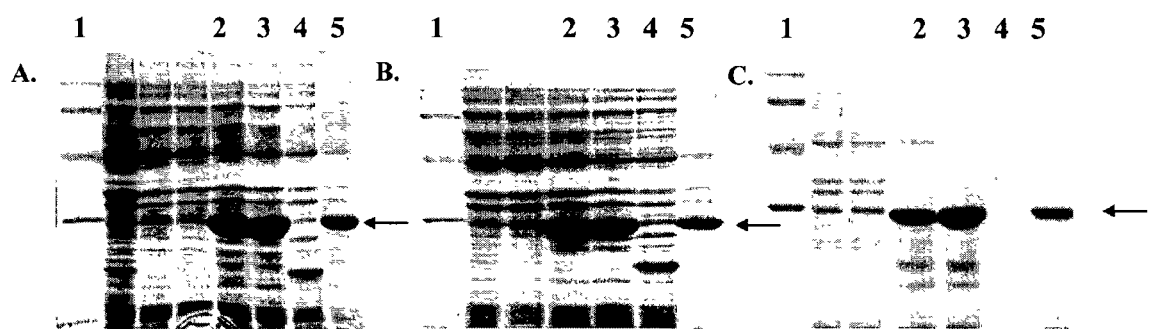

FIG. 2 shows the SDS-PAGE analysis of recombinant GST expression in different expression plasmids. The lanes are as follows:
 1. Protein molecular weight marker;
 2. IPTG induced expression of pTORG/BL21(DE3);
 3. IPTG induced expression of pTRG/BL21(DE3);
 4. IPTG induced expression of pET32a/BL21(DE3);
 5. IPTG induced expression of pALEX/BL21(DE3).

A: total cellular proteins; B: sonicated cellular supernatant fractions; C: sonicated cellular pellet fractions. Arrows indicate position of recombinant GST protein.

EXAMPLES

Example 1

Figure 1:
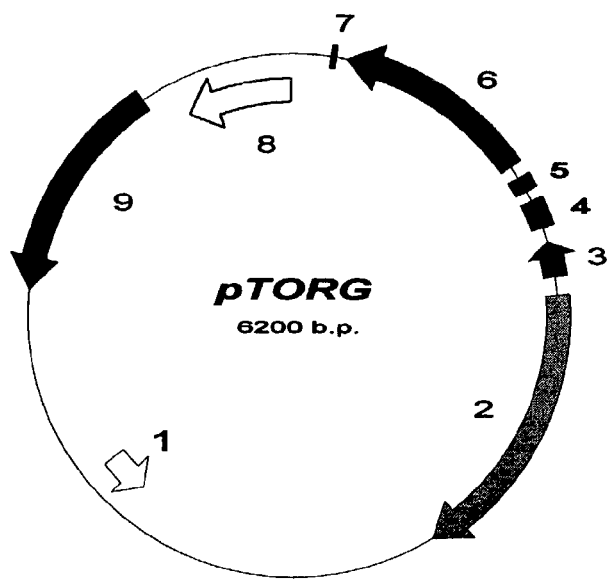
FIG. 1 shows the diagram of pTORG recombinant expression vector.

(1). Oligonucleotides were synthesized, annealed and ligated together to form the DNA fragment of omega leader sequence. The expression vector pTORG was constructed by introducing the omega leader sequence-containing fragment into pET32a (a universal expression vector commercially available from Novagen Company), and then by cloning the GST encoding gene, the multiple cloning sites, as well as the histidine tag coding region into the same plasmid. FIG. 1 shows the diagram of expression plasmid pTORG. Omega leader sequence was positioned between the T7 promoter and ribosome binding site. The core regulatory region consisted of T7 promoter and lac operator, omega leader sequence, ribosome binding site (SD sequence), GST coding region, multiple cloning sites, histidine tag coding region, and T7 terminator. The structure of said core regulatory region is as follows:

For comparison purposes, GST gene was also cloned into pET32a to obtain a normal control plasmid pTRG without the omega leader sequence. In addition, pALEX, a universal GST fusion expression vector, which is also driven by T7 promoter (Panagiotidis, C. A., Silverstein, S. J. Gene 164: 45–47, 1995), was employed.

(2). After transformation of all the three above recombinant expression plasmids into *E. coli* BL21 (DE3), the heterologous recombinant GST proteins were expressed by IPTG induction. The total cellular proteins, proteins in the soluble supernatant and insoluble pellet fractions were analyzed by SDS-PAGE on 12% dissolving gel and on 5% stacking gel, stained by Coomassie Blue R250 (FIG. 2). Quantitative densitometric scanning analysis of SDS-PAGE indicates that, the total GST products from original 0.3 ml culture were about 17.36 ug, 19.19 ug, 10.64 ug produced by pTORG, pTRG and pALEX, respectively. The cells were lysed by sonication; the supernatants were isolated by centrifugation. The soluble GST products in the supernatant from the same volume of culture were 14.09 ug, 9.6 ug, 6.09 ug expressed by pTORG, pTRG and pALEX, respectively. The soluble GST produced by pTORG, pTRG and pALEX were about 81.2%, 50% and 57.2% of the total expressed GST proteins, respectively. The expression level of recombinant GST by pTORG was 28% of the total cellular proteins, while the soluble GST was 35% of the cellular soluble fractions. The introduction of omega leader sequence into an expression vector almost does not influence the expression level of the recombinant proteins since the expression level of pTORG with omega leader sequence and that of pTRG without omega leader sequence are equivalent. Nevertheless, the yield of the soluble GST product of pTORG is 1.5 fold as much as that of pTRG.

In order to accurately validate the accuracy of the SDS-PAGE analysis, a more sensitive quantitative assay, GST enzymatic assay, was employed to determine the relative amount of active GST that appear in the cellular soluble supernatant fraction. As a result, the relative amount of active GST produced by pTORG, pTRG, pALEX are 115.2, 77.6, 72.1, respectively. It shows that the product of active GST with help of omega leader sequence in pTORG is 1.5 fold of that in pTRG, which does not contain the omega leader sequence. Therefore, this result further confirmed the conclusion in the SDS-PAGE analysis, and it also proved that the expressed soluble GST proteins were folded correctly and bioactive.

Moreover, the soluble active GST products were purified via affinity chromatography using Glutathione-Sepharose

```
                                                                              (SEQ ID NO:3)
T7 promoter-LacO-TCTAGATATTTTTACAACAATTACCAACAACACAAACAACAAACAACATTACA
                                       omega leader sequence Initiation codon
ATTACTATTTACAATAACAATGGCTAGAAATAATTTTGTTTAACTTTAAGAAGGAGATATACCATGGAA
                                   Ribosome binding site & SD sequence (SEQ ID NO:4)

ACAGTATTC-GST Coding region-ATCGAAGGTCGT GGGATCCCCGGGAATTCGAGCTCCGTCGAC
                   Coding region of Factor Xa cleavage site  multiple cloning sites Stop codon
AAGCTTGCGGCCGCACTCGAG CACCACCACCACCACCAC TGA---T7 terminator
   Coding region of histidine tag
```

4B column. The overall recovery yields of active GSTs were 26.6 mg of pTORG and 14.6 mg of pTGR from 200 ml of the culture. The GST yield of pTORG containing leader sequence was 1.8 fold as many as that of pTRG without omega leader sequence.

Example 2

To verify the solubility enhancing capability of GST-fusion expression vector pTORG, a GST-K5 fusion cassette was constructed and expressed. Kringle 5 (K5) domain of human plasminogen was obtained via PCR, using human plasminogen cDNA as template. The 308bp PCR product having sequence of SEQ ID NO: 5 was cloned between EcoR I and Xho I sites of multiple cloning sites of pTORG and of pTRG, thus forming GST-K5 fusion cassettes in both vectors, with or without omega leader sequence in their 5' untranslatable region, respectively. The resulting plasmids pTORG/K5 and pTRG/K5 were transformed into E. coli BL21 (DE3) and expressed under IPTG induction.

The 38.5KD fusion protein GST-K5 mainly appeared in soluble form. Densitometric scanning analysis showed that 79% of the produced GST-K5 (MW 38.5 KDa) existed in the soluble cell lysate in pTORG/K5, while only 55% being maintained in the soluble form in pTRG/K5. The overall recovery yields of GST-K5 after purification were 6.2 mg and 4.5 mg from 200 ml culture medium harboring pTORG/K5 and pTRG/K5, respectively. Together with the data from GST-activity assay, it was indicated that, the yield of soluble GST-K5 in pTORG/K5 was about 1.4 to 1.7 fold as much as that in the control plasmid pTRG/K5. It clearly showed that the solubility of GST-K5 was markedly increased with the help of omega leader sequence. This result was consistent with the data from the expression of reporter GST only, reinforcing the conclusion that the omega sequence could significantly enhance the solubility of heterogonous recombinant proteins in E. coli. The above data also suggested that the newly created plasmid pTORG was a potential and promising solubility-enhancing GST fusion expression vector.

In the examples of the invention, we employed three type of assays including the SDS-PAGE gel quantitative scanning analysis, GST enzymatic assay as well as yield determination by purification, to determine and to compare the capacity of the three vectors of producing soluble and active heterologous products. These three vectors include pTORG, which contains omega leader sequence, pTRG, which is in lack of the omega leader sequence, and ALEX, which is a universal GST fusion expression vector. The same conclusion drawn from these assays was that, the omega leader sequence could substantially increase yield of soluble and bioactive recombinant products in E. coli, effectively reduce formation of inclusion bodies. Therefore, it showed a promising practical value in biotechnology research and practice. Compared with the commonly used GST fusion plasmid pALEX, pTORG constructed in the examples was a more efficient and better GST fusion expression vector. By using said vector, one can construct fused expression cassette of any heterologous gene with GST gene, thereby obtaining the bioactive and high-soluble heterologous products in a GST-fusion form.

REFERENCES

1. Panagiotidis, C. A., Silverstein, S. J., "pALEX, a dual-tag prokaryotic expression vector for the purification of full-length proteins", Gene 164:45–47, 1995
2. Daniel R. Gallie et al. "Identification of the motifs within the tobacco mosaic virus 5'-leader responsible for enhancing translation", Nucleic Acids Research, Vol. 20, No. 17, 4631–4638, 1992
3. Kenneth Richards et al. "Nucleotide Sequence At The 5' Extremity Of Tobacco-Mosaic-Virus RNA", Eur. J. Biochem. 84, 513–519, 1978

What is claimed is:

1. An *E. coli* expression vector comprising an omega leader sequence between the promoter region and ribosome binding site, wherein the omega leader sequence comprises the sequence of SEQ ID NO: 2.

2. The expression vector of claim 1 comprising a core regulatory region having the sequence of SEQ ID NO: 1.

3. The expression vector of claim 1 which is a GST fusion expression vector.

4. An *E. coli* comprising the *E. coli* expression vector of claim 1.

5. A method for improving an *E. coli* expression vector comprising the steps of:
   (a) providing an *E. coli* expression vector which comprises an promoter region and ribosome binding site;
   (b) inserting an omega leader sequence between said promoter region and ribosome binding site, thereby forming an expression vector which comprises said omega leader sequence, wherein the omega leader sequence comprises the sequence of SEQ ID NO: 2.

6. The method of claim 5 which further comprises the step of:
   (c) inserting the GST coding sequence, the multiple cloning sites, and the histidine tag coding region orderly into said vector, downstream of the ribosome binding site, thereby forming a GST fusion expression vector.

7. The expression vector of claim 1, further comprising Shine-Dalgarno sequence.

8. The expression vector of claim 1, wherein the promoter comprises T7 promoter.

9. The method of claim 5, wherein the promoter comprises T7 promoter.

* * * * *